United States Patent [19]

Brajnovic et al.

[11] Patent Number: 5,087,200
[45] Date of Patent: * Feb. 11, 1992

[54] SPACER FOR DENTAL IMPLANTS

[75] Inventors: Izidor Brajnovic; Lars Jorneus, both of Gothenburg, Sweden

[73] Assignee: Nobelpharma AB, Gothenburg, Sweden

[*] Notice: The portion of the term of this patent subsequent to Mar. 19, 2008 has been disclaimed.

[21] Appl. No.: 614,134

[22] Filed: Nov. 16, 1990

Related U.S. Application Data

[63] Continuation of Ser. No. 417,091, Oct. 4, 1989, Pat. No. 5,000,685, which is a continuation of Ser. No. 195,334, May 18, 1988, Pat. No. 4,872,839.

[30] Foreign Application Priority Data

Jun. 12, 1987 [SE] Sweden ............... 8702445

[51] Int. Cl.$^5$ ............................................. A61C 8/00
[52] U.S. Cl. ..................................... 433/73; 433/174
[58] Field of Search ............... 433/169, 173, 174, 175, 433/176

[56] References Cited

U.S. PATENT DOCUMENTS

| | | | |
|---|---|---|---|
| 3,732,621 | 5/1973 | Bostrom | |
| 4,531,915 | 7/1985 | Tatum, Jr. | 433/173 |
| 4,547,157 | 10/1985 | Driskell | 433/173 |
| 4,645,453 | 2/1987 | Niznick | 433/173 |
| 4,713,003 | 12/1987 | Symington et al. | 433/173 |
| 4,713,004 | 12/1987 | Linkow et al. | 433/174 |
| 4,780,080 | 10/1988 | Harris | 433/174 |
| 4,842,518 | 6/1989 | Linkow et al. | 433/174 |
| 4,854,872 | 8/1989 | Detsch | 433/173 |
| 4,907,969 | 3/1990 | Ward | 433/173 |
| 5,000,685 | 3/1991 | Brajnovic | 433/173 |

FOREIGN PATENT DOCUMENTS

| | | |
|---|---|---|
| 0216031 | 4/1987 | European Pat. Off. . |
| WO83/00616 | 3/1983 | PCT Int'l Appl. . |
| WO88/03007 | 5/1988 | PCT Int'l Appl. . |

Primary Examiner—Cary E. O'Connor
Attorney, Agent, or Firm—Pollock, Vande Sande & Priddy

[57] ABSTRACT

The disclosure relates to a spacer for dental implants of a bio-compatible material. The spacer includes an inner sleeve-shaped spacer element (4) of titanium which is part of a screw connection between an anchorage element (fixture) (1) implanted in the maxillary beneath the gingiva, and a dental prosthesis construction whose joint surface (11) is located above the gingiva and which is disposed to absorb the loading of the screw connection. The spacer further includes an outer spacer sleeve (12) of porcelain or ceramics which wholly or partly encloses the inner sleeve-like spacer element (4). The ceramic or porcelain sleeve may, by grinding and coating with porcelain of different colors, by caused by visually approximate a dental cervix and gingiva and, thereby, not contrast with the natural dental cervix color and gingival color to the same extent as does the titanium material.

5 Claims, 1 Drawing Sheet

SPACER FOR DENTAL IMPLANTS

This application is a continuation of application Ser. No. 417,091, filed Oct. 4, 1989, now U.S. Pat. No. 5,000,685, which is a continuation of application Ser. No. 195,334, filed May 18, 1988, now U.S. Pat. No. 4,872,839.

TECHNICAL FIELD

The present invention relates to a spacer for dental implants of a bio-compatible material and constituting a connection element in a removable screw connection between an anchorage (fixture) implanted in the maxillary beneath the gingiva, and a dental prosthesis construction whose joint surface is located above the gingiva.

BACKGROUND ART

It is previously known in this art to permanently anchor all prostheses in the maxillary by means of helicoid anchorage elements, so-called fixtures, of a bio-compatible material, preferably pure titanium. The method which has displayed the highest degree of anchorage stability and which has successfully been used clinically for more than 20 years is the so-called osseointegration method developed by professor Per-Ingvar Brånemark et al and described in, for example, Brånemark/Zarb/Albrektsson: "Tissue-Integrated Prostheses", Quintessence Books, 1985.

The method is based on a highly exact and atraumatic implant technique of the fixture such that a direct contact—in other words an exact adaptation without interjacent soft tissue—occurs between the fixture and the bone tissue. Such a direct contact between fixture and bone tissue provides the best preconditions for a really permanent fixation of, for example, a dental prosthesis.

The helicoid fixtures of pure titanium are operated into the maxillary in a first surgical operation which is followed by an unloaded healing phase of critical length during which time the fixture is covered by intact mucous membrane. During this healing phase, the bone tissue grows onto and forms a unit with the implanted fixture. In a second operation, the fixture is then exposed and a substantially tubular spacer is applied to the fixture by means of a spacer screw. Subsequently, the dental prosthesis proper—in the form of a bridge construction—is united to the fixture by means of a fixing screw which, in its turn, anchors in the spacer screw.

. A bridge construction is anchored in place by means of a plurality of fixtures, for example six in number, and corresponding spacers which constitute connection elements between the bridge construction and the fixtures. To be able to absorb the extreme oral loadings to which the screw connection is subjected, the spacers are of a bio-compatible material of extremely good strength properties, for example titanium or the like.

Normally, the connection portion (base portion) of the spacer against the fixture will, after the operation, be enclosed by the gingiva. However, the major portion of the spacer will project up above the edge of the gingiva in that gap which is formed between the gingival edge and the joint surface of the bridge construction. Normally, such exposure of the spacer will seldom constitute an inconvenience, since the spacer is concealed behind the patient's lips. However, in certain cases when the lips are raised considerably, the spacers will also become visible during speech and normal mimicry, a factor which may be disconcerting for esthetic reasons, because of the visible contrast of the metal surface of the spacers against the surrounding dental cervix and gingival colour of the patient.

Even in those cases where such spaces are very seldom exposed to view, it may be psychologically disturbing for the patient. Nor is it possible to design the bridge construction in such a manner that it descends to the gingival edge and masks the spacers, since there must be a sufficiently wide gap or space between the gingival edge and the joint surface of the bridge construction about the spacer in order to make possible cleaning the interface zone between the implant material and the gingival tissue. Such cleaning is of vital importance to prevent occurrence of gingivitis, which may spread in the interface zone between the implant material and the bone tissue and jeopardize the anchorage of the dental implant.

OBJECT OF THE PRESENT INVENTION

The object of the present invention is to solve the above-outlined problems and design the spacer in such a manner that it will be less visually dominant in those cases when it is exposed to view. The present invention constitutes a solution to these problems, this solution being apparent from the characterizing clause of appended claim 1.

BRIEF DESCRIPTION OF THE ACCOMPANYING DRAWINGS

The nature of the present invention and its aspects will be more readily understood from the following brief description of the accompanying drawings, and discussion relating thereto.

DESCRIPTION OF PREFERRED EMBODIMENT

Figure 1:
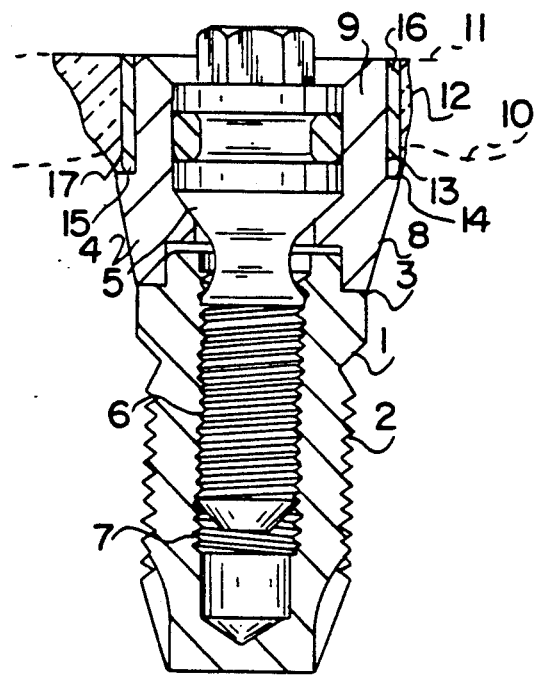
FIG. 1 is a section through a first embodiment of the present invention.

Referring to the Drawings, FIG. 1 shows an anchorage element in the form of a cylindrical screw 1 of titanium with an exterior thread 2 intended to be inserted in a predrilled hole in the maxillary for permanent anchorage of a dental prosthesis. A spacer has been connected to the upper portion 3 of the fixture, the spacer comprising a substantially tubular spacer element 4 also of titanium, and a spacer screw 5 provided with a threaded portion 6 which engages with an interiorally threaded bore 7 in the upper region of the fixture for fixedly anchoring the spacer 4 to the fixture.

Both the fixture and the spacer screw are of per se known design and will not, therefore, be described in greater detail here. Both consist of standard components included in Nobelpharma Implant System. However, the spacer has been modified as compared with prior art spacer members.

The spacer element 4 is provided with a lower, substantially conically tapering portion 8 for gingival penetration, and an upper cylindrical portion 9 which projects above the gingival edge 10 and extends from the above-mentioned conical portion up to the joint surface 11 of a prosthesis construction (dental bridge), not shown. The spacer element 4 is of pure titanium, which is of documented bio-compatibility and possesses moreover good strength properties, enabling it to absorb the forces of the screw connection.

Depending upon the conditions prevailing in the mouth, the cylindrical portion of the spacer element will, after mounting of the prosthesis construction, normally be exposed. As was mentioned by way of introduction, such exposure is also normal so as to permit cleaning about the spacer members. However, because the titanium in the spacer element is in stark contrast to the dental cervix colour and gingival colour, this may be esthetically disturbing to certain patients. Consequently, according to the present invention, at least the cylindrical portion of the spacer element 4 is provided with a coating of a tooth-like material, preferably ceramic or porcelain. This coating is designed as a sleeve 12 which may be loose and solely anchored to the spacer element 4 by a light clamping between prosthesis and spacer element. Because of the frangibility of such materials, the sleeve should not be subjected to any loading. Alternatively, the sleeve may be fused directly to the titanium in the spacer element.

The sleeve 12 of ceramics or porcelain may be ground and coated with porcelain of different colours at a dental technological laboratory for individual detail adaptation to the prevailing situation in the mouth of the patient. Sealing of the microscopic gaps in the joints between the sleeve 12 and the spacer element 4 may be effected using per se known bio-adapted jointing materials. In those cases where the sleeve is removable, the advantage will be gained that the tissue-sensitive spacer element will not be contaminated or otherwise negatively influenced during the dental technological process.

The spacer element 4 is preferably provided with a milled recess 13 for the spacer sleeve 12, the outer contour 14 of the porcelain/ceramics at the shoulder 15 in the milled recess being adapted to the outer contour of the spacer element.

As has been mentioned above, the spacer sleeve 12 may be loosely adapted to the spacer element 4 or be fused directly to the titanium therein. However, the porcelain/ceramics in the spacer sleeve is preferably disposed on a thin cylinder 16 of gold, aluminium oxide or similar material, as is apparent from both FIGS. 1 and 2. When necessary, a bevelling 17 is effected to the cylinder 16 at the connection to the shoulder 15 in the spacer element, such that the porcelain/ceramics connects directly to the titanium in the surface layer of the spacer element.

Figure 2:
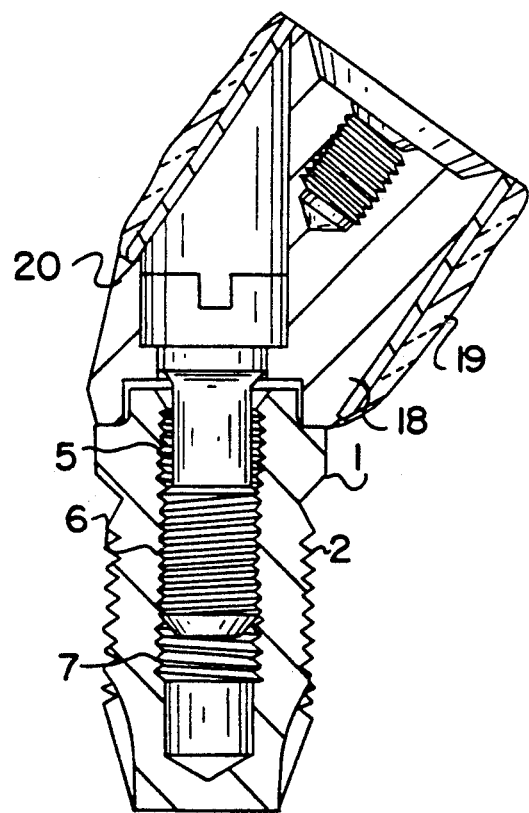
FIG. 2 shows an alternative embodiment in conjunction with an angled spacer.

FIG. 2 shows an example of an angled spacer element 18 with an external coating in the form of a spacer sleeve 19 of a type similar to that already described with reference to FIG. 1. In this case, the spacer sleeve 19 simultaneously constitutes a sealing against the screw passage 20 in the spacer element 18.

By designing the spacer element in the manner described above, the tissue in the innermost, most critical zone, will be contiguous with the titanium in the spacer element 4, while the sleeve 12 will be contiguous with the outer portion of the soft tissue and cover that portion of the spacer element 4 which projects above the gingival edge. The forces of the screw connection are absorbed by the spacer element 4, and connection of the dental prosthesis is effected above the gingival edge, as in existing systems. Hereby, the documented advantages of existing spacer systems will be retained, at the same time as the cosmetically advantageous coating may be inserted without giving rise to any problems of materials strength.

While the present invention is particularly intended for use in conjunction with bridge constructions, it may also be employed in single-tooth restorations. Prior art single-tooth constructions have entailed that the entire dental prosthesis is anchored directly on the fixture beneath the gingiva, which involves problems of adaptation and fit (concealed joint) and disturbances of the healing process of the gingiva against the spacer. According to the present invention, a separate spacer sleeve may be applied on the spacer element and the dental prosthesis proper may be tested and adapted without involving any problems of fit against the concealed joint beneath the gingival edge.

The present invention should not be considered as restricted to that described above and shown on the Drawings, many modifications being conceivable without departing from the spirit and scope of the appended claims.

What we claim and desire to secure by Letters Patent is:

1. An angulated spacer element adapted at its one end for attachment to a fixture defining therein a threaded aperture, said fixture being intended for implantation in the maxillary, and said spacer element being adapted at its other end to support a dental prosthesis, said spacer element comprising:

a unitary member having a first portion with an end surface thereof permitting abutting engagement with the protruding end of the implanted fixture, said first portion also having a through bore defining an internal ledge to enable a screw to pass through said bore, abut said ledge, and threadably engage the threaded aperture in the fixture; and said unitary member having a second portion having means for supporting and securing to said unitary member said dental prosthesis, said second portion forming an acute angle with respect to said through bore.

2. The spacer element of claim 1, in which said through bore defines an opening extending through the wall of said second portion.

3. The spacer element as claimed in claim 2, further comprising:

a covering sleeve adapted for insertion over said second portion of said unitary member to cover said opening.

4. The spacer element as claimed in claim 3, wherein said covering sleeve abuts against an outwardly-extending flange formed between said first and second portion of said unitary member.

5. The spacer element as claimed in claim 4, wherein said covering sleeve is made of porcelain or ceramics.

* * * * *

REEXAMINATION CERTIFICATE (2869th)
United States Patent [19]

Brajnovic et al.

[11] B1 5,087,200

[45] Certificate Issued * May 7, 1996

[54] SPACER FOR DENTAL IMPLANTS

[75] Inventors: Izidor Brajnovic; Lars Jorneus, both of Gothenburg, Sweden

[73] Assignee: Nobelpharma AB, Gothenburg, Sweden

Reexamination Request:
No. 90/003,577, Sep. 19, 1994

Reexamination Certificate for:
Patent No.: 5,087,200
Issued: Feb. 11, 1992
Appl. No.: 614,134
Filed: Nov. 16, 1990

[*] Notice: The portion of the term of this patent subsequent to Mar. 19, 2008, has been disclaimed.

Related U.S. Application Data

[63] Continuation of Ser. No. 417,091, Oct. 4, 1989, Pat. No. 5,000,685, which is a continuation of Ser. No. 195,334, May 18, 1988, Pat. No. 4,872,839.

[30] Foreign Application Priority Data

Jun. 12, 1987 [SE] Sweden ............................ 8702445

[51] Int. Cl.$^6$ ........................................ A61C 8/00
[52] U.S. Cl. ............................. 433/173; 433/174
[58] Field of Search ........................ 433/173, 174, 433/175, 176

[56] References Cited

U.S. PATENT DOCUMENTS

| | | |
|---|---|---|
| 3,067,740 | 12/1962 | Haboush . |
| 3,732,621 | 5/1973 | Bostrom . |
| 3,987,499 | 10/1976 | Scharbach et al. . |
| 4,177,562 | 12/1979 | Miller et al. ............................ 433/174 |
| 4,187,559 | 2/1980 | Grell et al. . |
| 4,416,629 | 11/1983 | Mozsary et al. ........................ 433/174 |
| 4,531,915 | 7/1985 | Tatum, Jr. ............................... 433/173 |
| 4,547,157 | 10/1985 | Driskell .................................. 433/173 |
| 4,693,724 | 9/1987 | Rhenter et al. ......................... 623/23 |
| 4,822,370 | 4/1989 | Schelhas ................................. 623/23 |
| 5,015,186 | 5/1991 | Detsch .................................... 623/23 |
| 5,080,685 | 1/1992 | Bolesky et al. ......................... 623/23 |
| 5,181,928 | 1/1993 | Bolesky et al. ......................... 623/23 |

FOREIGN PATENT DOCUMENTS

| | | |
|---|---|---|
| 2576793 | 8/1986 | France . |
| 2413883 | 9/1975 | Germany . |

*Primary Examiner*—Cary E. O'Connor

[57] ABSTRACT

The disclosure relates to a spacer for dental implants of a bio-compatible material. The spacer includes an inner sleeve-shaped spacer element (4) of titanium which is part of a screw connection between an anchorage element (fixture) (1) implanted in the maxillary beneath the gingiva, and a dental prosthesis construction whose joint surface (11) is located above the gingiva and which is disposed to absorb the loading of the screw connection. The spacer further includes an outer spacer sleeve (12) of porcelain or ceramics which wholly or partly encloses the inner sleeve-like spacer element (4). The ceramic or porcelain sleeve may, by grinding and coating with porcelain of different colors, by caused by visually approximate a dental cervix and gingiva and, thereby, not contrast with the natural dental cervix color and gingival color to the same extent as does the titanium material.

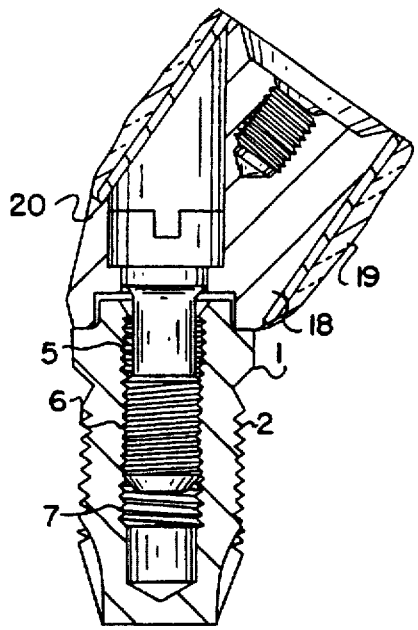

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–5 is confirmed.

* * * * *